United States Patent [19]
Hirschfeld

[11] Patent Number: 4,737,343
[45] Date of Patent: Apr. 12, 1988

[54] GAS-SENSING OPTRODE

[75] Inventor: Tomas B. Hirschfeld, Livermore, Calif.

[73] Assignee: The Regents of the University of California, Berkeley, Calif.

[21] Appl. No.: 820,122

[22] Filed: Jan. 21, 1986

[51] Int. Cl.$^4$ .................. G01N 21/77; G01N 33/497
[52] U.S. Cl. ..................................... 422/63; 436/133; 436/138; 436/163; 436/164; 436/172; 128/633; 128/643
[58] Field of Search .................. 422/68, 83, 91, 58; 436/166, 165, 167, 168, 163, 172; 128/633, 634

[56] References Cited

U.S. PATENT DOCUMENTS

| | | | |
|---|---|---|---|
| Re. 31,879 | 5/1985 | Lubbers et al. | 436/133 |
| 3,814,081 | 6/1974 | Mori | 128/634 |
| 3,929,605 | 12/1975 | Lubbers et al. | 204/128 |
| 4,050,450 | 9/1977 | Polanyi et al. | 128/634 |
| 4,201,222 | 5/1980 | Haase | 128/634 |
| 4,272,484 | 6/1981 | Lubbers | 422/58 |
| 4,272,485 | 6/1981 | Lubbers | 422/68 |
| 4,440,620 | 4/1984 | Ono et al. | 204/403 |
| 4,476,870 | 10/1984 | Peterson et al. | 128/634 |
| 4,548,907 | 10/1985 | Seitz et al. | 422/68 X |

FOREIGN PATENT DOCUMENTS 0072627  2/1983  European Pat. Off.

Primary Examiner—Michael S. Marcus
Assistant Examiner—Timothy M. McMahon
Attorney, Agent, or Firm—Stephen C. Macevicz; Michael B. K. Lee; Henry P. Sartorio

[57] ABSTRACT

An optrode is provided for sensing dissolved gases or volatile components of a solution. A fiber optic is provided through which light from an associated light source is transmitted from a first end to a second end. A bubble forming means, such as a tube, is attached to the second end of the fiber optic, and an indicator material is disposed in cooperation with the bubble forming means adjacent to the second end of the fiber optic such that it is illuminated by light emanating from the second end. The bubble forming means causes a gas bubble to form whenever the optrode is immersed in the fluid. The gas bubble separates the indicator material from the fluid. Gases, or other volatile components, of the fluid are sensed as they diffuse across the gas bubble from the fluid to the indicator material.

8 Claims, 3 Drawing Sheets

GAS-SENSING OPTRODE

BACKGROUND OF THE INVENTION

The United States Government has rights in this invention pursuant to Contract No. w-7405-ENG-48 between the U.S. Department of Energy and the University of California, for the operation of Lawrence Livermore National Laboratory.

The invention relates to optical means for remotely monitoring the concentration of dissolved gases, and in particular to a mechanical means for preventing contact of gas-sensitive indicators with the gas-containing solution.

The measurement of dissolved gases, particularly in aqueous solutions is highly useful in medical, industrial, and environmental settings. For example, carbon dioxide and oxygen concentrations in the blood are critical indicators of respiratory function; dissolved oxygen in boiler feed water can be highly corrosive; oxygen and carbon dioxide content are critical parameters in fermentation media; and oxygen content is important in sewage treatment, and is an indicator of the degree of stagnation in ponds, lakes, and the like.

Optical methods for measuring dissolved oxygen concentration based on fluorescence quenching is well known, e.g., Stevens, U.S. Pat. No. 3,612,866, issued Oct. 12, 1971, entitled, "Instrument for Determining Oxygen Quantities by measuring Oxygen Quenching of Fluorescent Radiation." However, a general problem associated with the use of colorimetric or fluorescent probes for oxygen, and other dissolved gases or volatile components, is the interfering effects of the solvent in which the gases are dissolved, or the interfering effects of other solutes or contaminants in the solution. This is particularly troublesome when such probes are employed for medical monitoring because of the interfering effects of the body's immune responses.

Buckles, in U.S. Pat. No. 4,399,099, issued Aug. 16, 1983, entitled "Optical Fiber Apparatus for Quantitative Analysis," discloses the detection of dissolved oxygen gas by a sensor comprising a fiber optic having a section of cladding replaced by two concentric coatings, the innermost coating containing an oxygen-quenchable fluorescent dye and the outermost coating being selectively permeable to oxygen, and impermeable to contaminating agents.

Petersen et al., in U.S. Pat. No. 4,476,870, issued Oct. 16, 1984, entitled "Fiber Optic $pO_2$ Probe," disclose the use of oxygen quenchable fluorescent dyes embedded on absorbent particles held adjacent to the end of a fiber optic by a closed membrane jacket, or tube. Petersen et al. teach the use of a water impermeable jacket.

Lubbers et al., in U.S. Pat. No. Re. 31,879, issued May 7, 1985, entitled "Method and Arrangement for Measuring the Concentration of Gases," disclose the use of semipermeable membranes to contain an indicator means responsive to selected gases dissolved in a sample fluid.

SUMMARY OF THE INVENTION

Apparatus and methods of its use are provided which employ fluorescent and/or colorimetric indicators to monitor concentrations of dissolved gases, or other volatile components of a sample fluid. The apparatus is referred to as an "optrode". A fiber optic is provided through which light from an associated light source is transmitted from a first end of the fiber optic to a second end of the fiber optic. An indicator material, fluorescent, colorimetric, or the like, is held adjacent to the second end of the fiber optic so that light emanating from the second end illuminates at least a portion of the indicator material. The indicator material need not be in contact with the second end of the fiber optic. Finally, a bubble forming means is attached to the second end of the fiber optic, the bubble forming means causing a gas bubble to form at the second end whenever the second end is immersed in a sample fluid. The gas bubble produced by the bubble forming means serves to separate the indicator material from the sample fluid.

A preferred bubble forming means is a tube coaxially attached to the second end of the fiber optic such that a fixed, airtight seal is formed. Inside the tube the indicator material is held adjacent to the second end of the fiber optic. The tube attached to the second end of the fiber optic is long enough so that a gas bubble forms in the tube whenever the fiber optic and tube are immersed in a sample fluid.

Gases, or other volatile components, of the sample fluid are sensed as they diffuse across the gas bubble from the sample fluid to the indicator material.

The present invention is addressed to problems of remotely monitoring dissolved gases or other volatile components of sample fluids of medical, industrial, or environmental interest. It overcomes the problem of indicator inactivation, caused by direct contact with the sample fluid, by providing a bubble forming means which separates the indicator material from the sample fluid. The gas bubble is a superior means for separation than semipermeable membranes because there is less likelihood of sensor inactivation due to fouling by accumulation of particulate matter, or by immune responses in the case of medical uses. Moreover, the preferred forms of the bubble forming means are easily and inexpensively constructed.

DETAILED DESCRIPTION OF THE INVENTION

The invention is an apparatus and method for separating indicator materials from sample fluids having volatile components, such as dissolved gases, which are to be sensed. The separation serves to protect the indicator materials from direct contact with the sample fluid or its non-volatile components which may cause inactivation. The separation also protects the sample fluid from contamination by the indicator materials, a major concern in connection with medical uses.

In accordance with the present invention a bubble forming means is attached to the end of a fiber optic (hereafter referred to as the second end of the fiber optic) An indicator material is held adjacent to the second end of the fiber optic such that light emanating from the fiber optic illuminates at least a portion of the indicator material. Fluorescent indicator materials are preferred because the illumination, or excitation, wavelength is different from the emission, or signal, wavelength for this class of indicators. The differences in wavelength permits the use of a single fiber optic for both illumination and signal collection because the signal can be readily separated from back-scatter generated by the illumination beam on the basis of wavelength differences.

Bubble forming means can be constructed using both mechanical and chemical techniques. The particular technique chosen or combination of techniques, depends in part on the application contemplated. A trade-off exists between forming gas bubbles having maximal bubble-sample fluid interface area and forming bubbles having maximal stability against mechanical stresses such as rapid pressure changes, sample fluid movement, turbulence, or the like. A large interface area-to-gas bubble volume ratio is preferred for higher response times. Yet in environments where there is turbulence or high velocity flows, it may be necessary, and preferable, to accept a reduced interface area-to-gas bubble volume ratio in exchange for increased mechanical stability of the gas bubble. Below, several embodiments of the invention are described which have alternative bubble forming means each exemplifying a different way in which the above-mentioned trade-off can be implemented.

Figure 1:
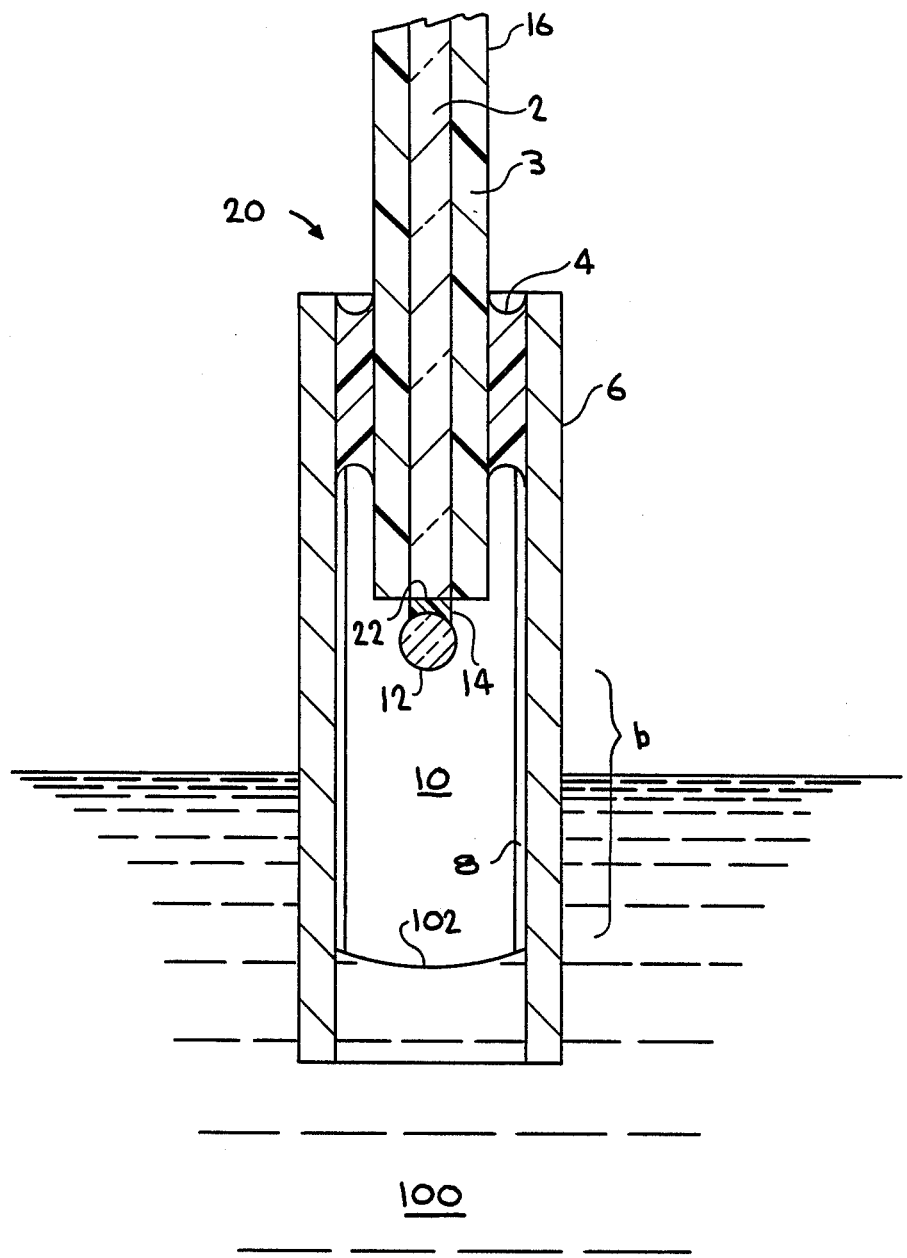
FIG. 1 is a cross-sectional view of an embodiment wherein the indicator material is carried by a solid support material attached to the end of the fiber optic.

FIG. 1 illustrates one preferred embodiment of the invention. Tube 6 is coaxially attached to second end 20 of fiber optic 16 by attachment means 4, which may be an adhesive, such as epoxy, a wax, a welded seal, or the like. The attachment may be between tube 6 and cladding 3 (as shown), or the attachment may be directly to core 2 of the fiber optic (such attachment not being shown). A fixed airtight seal is formed between tube 6 and fiber optic 16 to prevent the destruction of gas bubble 10 (which is formed in tube 6 upon immersion) in the event of mechanical disturbances.

Figure 3:
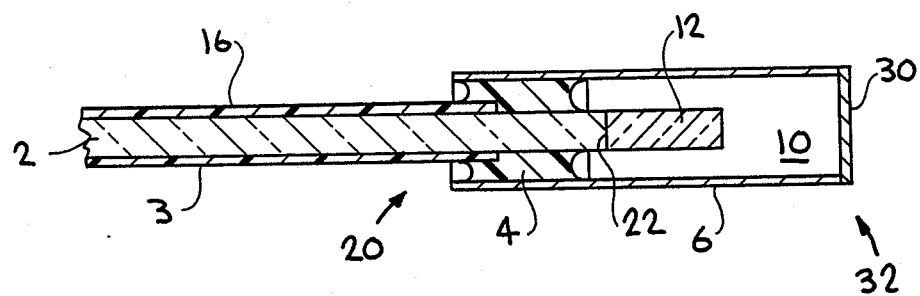
FIG. 3 is a cross-sectional view of an embodiment whose bubble forming means include a porous hydrophobic membrane cap on the end of a tube.

Solid support 12, e.g. in the form of a particle hereinafter referred to as a carrier particle, is attached to end face 22 of core 2 of fiber optic 16 by attachment means 14, which for example is epoxy adhesive, or the like. Alternatively carrier particle 12 may be in the form of a cylindrical piece of controlled pore glass welded onto end face 22 of core 2 of fiber optic 16, e.g. as shown in FIGS. 3 and 4.

The purpose of the carrier particle is to hold the indicator material and any reagents necessary for its use, such as anti-oxidants to reduce photo-bleaching of fluorescent indicators, or the like. The indicator may be adsorbed onto the carrier particle or covalently bonded to it. Techniques for attaching indicator molecules to solid supports are well-known, e.g., Mosbach, ed. *Methods in Enzymology*, Vol. 44, entitled "Immobilized Enzymes" (Academic Press, New York, 1976).

Preferably coating 8 is applied to the inner wall of tube 6 to enhance the formation of gas bubble 10. For example, in the case of aqueous sample fluids, such as blood, a hydrophobic coating is preferred. If tube 6 is glass such a coating may be applied by treatment with polymethylhydrosiloxane, which is available from Petrarch Systems, Inc. (Bristol, PA), or other procedures for siliconizing glassware, e.g., Schlief et al. *Practical Methods in Molecular Biology* (Springer-Verlag, New York, 1981), page 174.

When fiber optic 16 and attached tube 6 are immersed in sample fluid 100 gas bubble 10 forms inside tube 6. Gases or volatile components diffuse across bubble-sample fluid interface 102 and to the indicators held by carrier particle 12.

Figure 2:
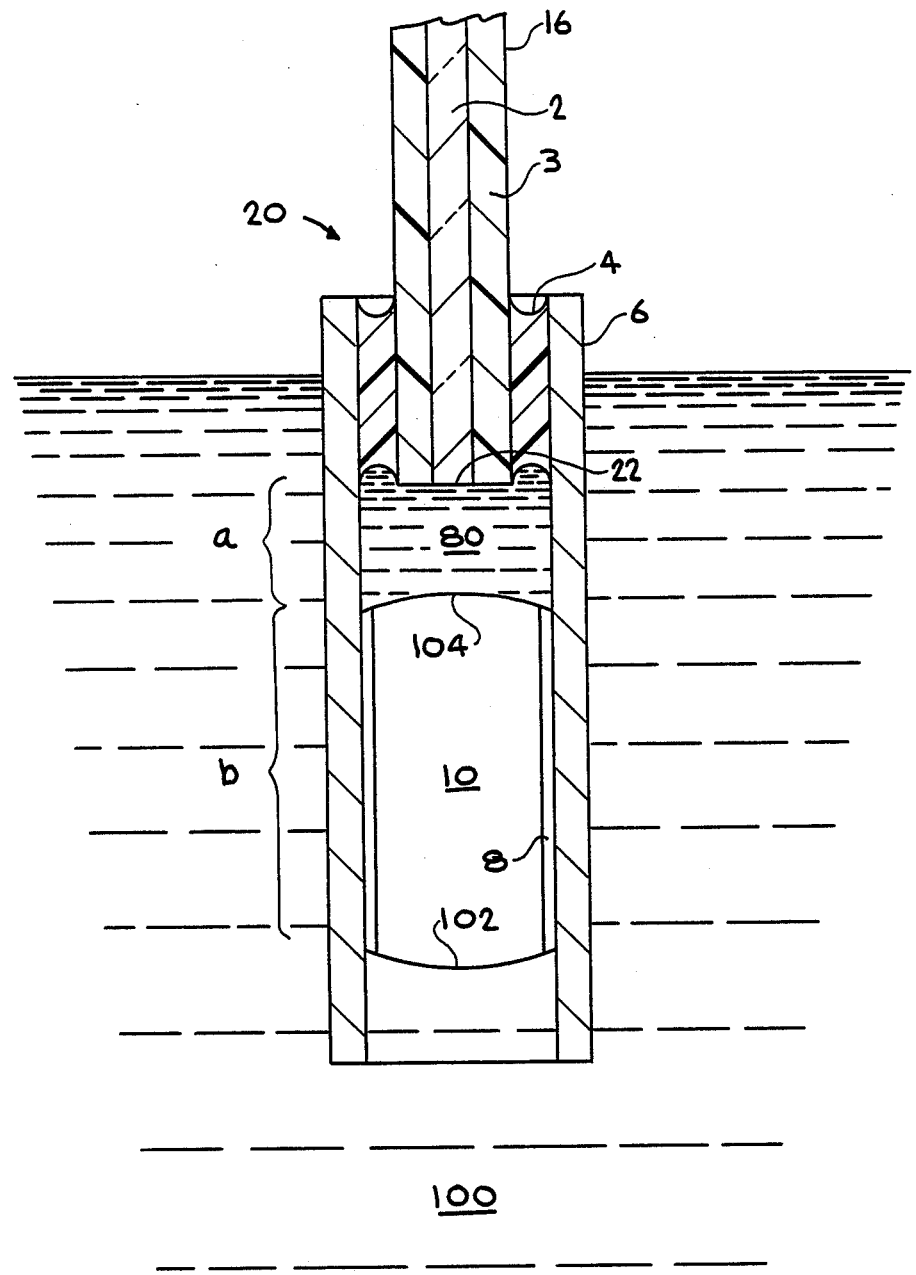
FIG. 2 is a cross-sectional view of an embodiment wherein the indicator material is in the form of a liquid reagent.

FIG. 2 illustrates another preferred embodiment of the invention in which the indicator material is dissolved in liquid reagent 80, which forms bubble-reagent interface 104. The numbers otherwise indicate the same features as described by the corresponding numbers in FIG. 1. The linear dimensions indicated by "a" and "b" in the figures are, respectively, the distance between the end face 22 of fiber optic 16 and the bubble-reagent interface 104, and the distance between carrier particle 12 (or bubble-reagent interface 104) and bubble-sample fluid interface 102. The exact values of these dimensions are not crucial to the invention; however, the response time of a sensor employing the present invention depends on the rate of diffusion of the gases or volatile components of interest across distance "b", and the case of embodiment of FIG. 2, response time may also depend on the rate of diffusion of the gases or volatile components within liquid reagent 80. Preferably, in the case of the embodiment of FIG. 2, "a" is as small as possible consistent with the generation of a detectable signal from the indicator.

FIG. 3 illustrates another preferred embodiment of the invention in which the bubble forming means comprises tube 6 coaxially attached to second end 20 of fiber optic 16, as in FIGS. 1 and 2. In addition, porous membrane 30 is sealingly attached to distal end 32 of tube 6, to form a cap. (Similarly numbered features in the figures refer to identical elements.) Preferably porous membrane 30 is a hydrophobic screen type filtration membrane, such as a Durapore (tradename of Millipore Corporation, Bedford, Mass.) membrane, which is made of polyvinylidene fluoride. Roughly the membrane can be viewed as a large collection of capillary sized channels between the interior of tube 6 and the sample fluid. The many small diameter channels in place of a single large diameter channel (consisting of the bore of tube 6) increases the mechanical stability of gas bubble 10 by reducing the area over which the surface tension of the sample fluid needs to act to maintain gas bubble 10. The average pore size of porous membrane 30 is sufficiently large so that no selective permeability occurs between the dissolved gases or volatile components of the sample fluid.

The detection apparatus and light sources required to operate the invention are well-known, e.g., Hirschfeld, U.S. Pat. No. 4,509,370 and 4,542,987, which are incorporated by reference for their descriptions of light sources and associated optics suitable for use with optrodes.

In operating the invention with fluorescent dyes photo-bleaching of the dye can rapidly degrade fluorescence output if the dyes are excited at too high power for prolonged period. The photo-bleaching problem can be greatly reduced, or even eliminated by reducing illumination beam power to the microwatt range, preferably from about 1 to 5 microwatts, and by shuttering the illumination beam so that the dye is illuminated for only short periods of time between longer intervals of nonillumination. The durations of the periods of illumination and nonillumination depend on the dye used and the power of the illumination beam. In the case of oxygen-quenchable fluorescent dyes, low power excitation and shuttering can prevent spurious results that arise from oxygen binding by the dyes.

The following examples serve to illustrate the present inventions. The particular kinds of indicators and reagents, their concentrations, and the values of other variable parameters are meant only to exemplify application of the present invention and are not to be considered limitations thereof.

EXAMPLE I

Oxygen-Sensing Optrodes

Two embodiments of the invention are described for sensing dissolved oxygen. The first employs indicator materials held on a carrier particle, as illustrated in FIG. 1, and the second employs indicator materials in solution, as illustrated in FIG. 2.

In the first oxygen-sensing optrode carrier particle 12 is soaked for about 2 hours in a solution comprising 40 g ethanol, 0.1 g Pylakrome Fluorescent Yellow 125781 (a trademarked product available from Pylam Products Co., Inc., Garden City, N.Y.), and 0.3 g polyvinyl pyrolidone. This solution corresponds to a dye concentration of about 2500 ppm. Operable embodiments have been constructed with dye concentrations in the range of 5–10,000 ppm. The optrode was tested in a controlled atmosphere instrument at 99% relative humidity under various concentration of oxygen. Table I lists the results. The carrier particle was continuously illuminated at 1 microwatt of 488 nm light (generated by an Argon ion laser). No photo-bleaching was observed at this power level.

TABLE I

Signal levels for Pylakrome Fluorescent Yellow Indicator for Various Oxygen Concentrations

| Oxygen Concentration | Signal (CDS) | % Change in Signal from Pure $N_2$ |
|---|---|---|
| 0% (pure $N_2$) | 23,000 | — |
| 4% $O_2$, 96% $N_2$ | 21,000 | 9% drop |
| 8% $O_2$, 92% $N_2$ | 18,600 | 19% drop |
| 20% $O_2$ (in air) | 16.300 | 29% drop |

A second oxygen-sensing optrode was constructed by placing a slurry of cellulose acetate containing flavin mononucleotide at a concentration of $4 \times 10^{-4}$M, in tube 6 as illustrated in FIG. 2.

EXAMPLE II

Carbon Dioxide-Sensing Optrode

The carbon dioxide-sensing optrode employs a pH-sensitive fluorescent dye in an aqueous solution, as illustrated in FIG. 2. Carbon dioxide changes the pH of the solution by reacting with water to form carbonic acid, which then dissociates liberating a hydrogen ion according to the following equations:

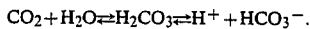

$$CO_2 + H_2O \rightleftharpoons H_2CO_3 \rightleftharpoons H^+ + HCO_3^-.$$

Increasing the amount of carbon dioxide drives the reaction to the right which lowers the pH, which is measured by the pH-sensitive fluorescent dye.

The descriptions of the foregoing embodiments of the invention have been presented for purposes of illustration and description. They are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. An optrode for monitoring dissolved gas concentration in a sample fluid, the optrode comprising:
   a fiber optic through which an illumination beam from an associated light source is transmitted from a first end of the fiber optic to a second end of the fiber optic;
   an indicator material adjacent to the second end of the fiber optic such that light from the illumination beam emanating from the second end of the fiber optic illuminates a portion of the indicator material causing it to produce an optical signal related to the dissolved gas concentration; and
   bubble forming means attached to the second end of the fiber optic for creating a gas bubble enclosing the indicator material whenever the second end of the fiber optic is immersed in a sample fluid, the gas bubble separating the indicator material from the sample fluid.

2. The optrode according to claim 1 wherein said bubble forming means is a tube coaxially attached to said second end of said fiber optic such that an airtight seal is formed and such that said indicator material is enclosed by the tube.

3. An optrode according to claim 2 wherein said tube is capped by a porous membrane.

4. An optrode according to claim 3 wherein said porous membrane is a hydrophobic screen type filtration membrane.

5. An optrode according to claim 2 wherein said inside surface of said tube is coated with a sample-fluid repelling substance for enhancing formation of said gas bubble.

6. An optrode according to claim 5, wherein said sample fluid is an aqueous solution, and wherein said coating of sample-fluid repelling substance is a hydrophobic coating.

7. An optrode according to claim 2 wherein said indicator material is dissolved in a liquid adjacent to and in contact with said second end of said fiber optic.

8. An optrode according to claim 1 wherein said indicator material is immobilized on a carrier particle attached to said second end of said fiber optic.

* * * * *